United States Patent [19]

Heinzerling

[11] 4,236,080
[45] Nov. 25, 1980

[54] X-RAY APPARATUS FOR COMPUTED TOMOGRAPHY

[75] Inventor: Jürgen Heinzerling, Hamburg, Fed. Rep. of Germany

[73] Assignee: U.S. Philips Corporation, New York, N.Y.

[21] Appl. No.: 5,745

[22] Filed: Jan. 23, 1979

[30] Foreign Application Priority Data

Jan. 23, 1978 [DE] Fed. Rep. of Germany ....... 2802746
Feb. 9, 1978 [DE] Fed. Rep. of Germany ....... 2805329

[51] Int. Cl.² ............................................. G03B 41/16
[52] U.S. Cl. ......................... 250/445 T; 250/416 TV
[58] Field of Search .................... 250/445 T, 416 TV

[56] References Cited

U.S. PATENT DOCUMENTS 4,135,096  1/1979  Giordano ......................... 250/445 T
4,160,167  7/1979  Weiss ............................... 250/445 T

OTHER PUBLICATIONS

"Spatial Filtering to Improve Transverse Tomography", Peters, IEEE Transactions of Biomedical Engr. Vol. BME 21, No. 3, May, 1974.

Primary Examiner—Craig E. Church
Attorney, Agent, or Firm—Thomas A. Briody; Robert T. Mayer; Jack E. Haken

[57] ABSTRACT

X-ray apparatus for computer tomography. Strip-shaped visible images which correspond to the individual X-ray exposures in one image plane are transferred to the light-sensitive input of an image pick-up tube by means of a lens system. The lens system comprises at least one lens, interposed between the image plane and the light-sensitive input layer of the image pick-up tube, which produces an astigmatic optical path.

10 Claims, 5 Drawing Figures

X-RAY APPARATUS FOR COMPUTED TOMOGRAPHY

The invention relates to an X-ray apparatus for computed tomography, in which the strip-shaped visible images which correspond to the individual X-ray exposures in one image plane are transferred to a light-sensitive input layer of an image pick-up tube by a lens system.

Such an arrangement is known from German Offenlegungsschrift 26 22 177 which corresponds to U.S. Pat. No. 4,160,167. A body is irradiated in a plurality of coplanar directions by a flat X-ray beam so as to obtain the individual X-ray images (projections). The X-ray beams are consecutively incident on an X-ray image intensifier, which produces strip-shaped visible images corresponding to the X-ray beams cross-section in the image plane on its output side. The images are also imaged in strip-form on a light-sensitive input layer of an image pick-up tube by a spherical lens. Electrical signals on the output of the image pick-up tube are characteristic of the absorption of the irradiated body layer and are available for the reconstruction of a computer tomography image. The signals are obtained through line-by-line scanning of the light-sensitive input layer. The line direction and the longitudinal direction of the image are the same.

As the height of the image on the light-sensitive input layer i.e. the dimension of the image perpendicular to the longitudinal direction substantially corresponds to the width of one line, i.e. (the line dimension perpendicular to the line direction) the line width being adjustable by focussing and deflecting the electron beam which scans the input layer, only a fraction of the light-sensitive input layer of the image pick-up tube, which in total comprises substantially more lines, for example 625 lines) is exposed. The rest of the input layer remains unexposed. The average electrical output signal of the image pick-up tube is consequently comparatively small, so that the output signal/noise ratio of the image pick-up tube is small. Moreover, in the case of a very small exposed area the output signal may be invalidated by differences in the sensitivity of the light-sensitive input layer.

It is an object of the invention to provide an arrangement for transferring strip-shaped visible images which are disposed in one image plane to a light sensitive input layer of an image pick-up tube which yields an improved output signal/noise ratio and which prevents invalidation of the output signal as a result of differences in the sensitivity of the light-sensitive input layer.

According to the invention this object is achieved in that the lens system comprises at least one lens which produces an astigmatic optical path and which is arranged between the image plane and the light-sensitive input layer of the image pick-up tube, by means of which lens the images can be transferred to the light-sensitive input layer so as to be focussed in their longitudinal direction and defocused in a direction perpendicular to the longitudinal direction.

The lens which produces an astigmatic optical path ensures that the transferred image is focused in its longitudinal direction and is sufficiently defocused in the perpendicular direction so that the total surface area of the light-sensitive input layer is at least approximately filled. In conjunction with an increased gain of the X-ray image intensifier this yields a substantial improvement of the output signal/noise ratio, because the average input signal of the image pick-up tube, which depends on the magnitude of the exposed input layer and the light intensity, increases as the utilization of the area of the light-sensitive input layer increases.

In accordance with a further embodiment of the invention the lens takes the form of a plano-convex or biconvex cylindrical lens, the cylinder axis being disposed perpendicular to the longitudinal direction of the images and extending perpendicularly through the optical system axis, which ensures that the images can be transferred to the light-sensitive input layer of the image pick-up tube in a simple and substantially distortion-free manner.

In accordance with a further embodiment of the invention the line direction of the image pick-up tube is disposed parallel to the cylinder axis. This ensures that the images are defocussed parallel to the line direction of the image pick-up tube and can thus be read line by line, each line illuminated by the defocussed image defining one image point. Thus, an image-point information value which is characteristic of the absorption of the body layer may be obtained by scanning one line, in that for example the average value of the output signal of the image pick-up tube per line is determined. In this way fluctuations in the output signal of the image pick-up tube as a result of local differences in sensitivity of the light-sensitive layer are averaged out. Averaging can be effected in known manner in that the output signal is for example passed through a low-pass filter.

Curvilinearly defocussed image points of an image may cover a plurality of lines, for example if the transfer is not distortion-free. However, reading such images does not give rise to any problems, because for a given optical path for example the path of the scanning electron beam of the image pick-up tube may be controlled electronically in conformity with the defocussed image points in known manner.

In accordance with a further embodiment of the invention there is interposed an optical image intensifier between the lens and the input layer of the image pick-up tube, whose output image may be transferred to the input layer of the image pick-up tube by means of a spherical lens.

Visible images which are produced by conversion of X-rays via X-ray fluorescent screens, have a comparatively low brightness. For nevertheless obtaining a sufficient light intensity, which results in a large output signal/noise ratio of the image pick-up tube, the defocussed images are first transferred to an optical image intensifier, which on its output side produces an intensified visible image.

Furthermore, by arranging the radiation intensifying elements (for example the optical image intensifiers or X-ray image intensifiers) in the radiation path the intensity of the X-radiation may be reduced, so that the dose administered to the patient may also be reduced.

In accordance with a further embodiment of the invention there is interposed a light-deflecting element between the lens and the image pick-up tube, by means of which element the individual images can be imaged consecutively onto the input layer of the image pick-up tube, so that their longitudinal sides are disposed parallel to and spaced from each other. Such a light deflecting element may take the form of a plane mirror, a polygonal mirror, or a prism which is rotatable about an axis.

The invention will now be described by way of example with reference to the drawing. In the drawing.

Figure 1:
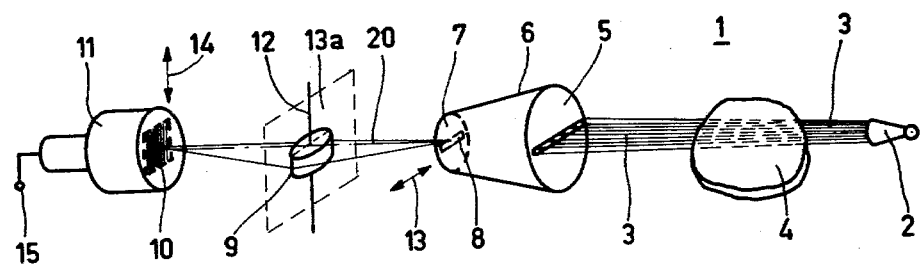
FIG. 1 is X-ray apparatus comprising a cylindrical lens which produces an astigmatic optical path.

FIG. 1 shows an X-ray recording apparatus with an X-ray source 2 from which a divergent X-ray beam 3 emerges. The beam extends in one plane and is collimated by diaphragms (not shown). The beam passes through a body slice 4 and is incident on an input face 5 of an X-ray image intensifier 6. In the image plane 7 at the output side of the X-ray image intensifier 6 a strip-shaped visible image 8 is formed which corresponds to the cross-section of the X-ray beam 3. The image is considerably reduced relative to the cross-section of the X-ray beam 3 which is incident on the input face 5 of the X-ray image intensifier 6. By means of a lens 9 (which takes the form of a biconvex cylindrical lens and which produces an astigmatic optical path) the image 8 is transferred to the input layer 10 of an image pick-up tube 11. The input layer 10 is disposed parallel to the image plane 7. The lens 9 is arranged so that its cylinder axis 12 is disposed both perpendicular to the longitudinal direction 13 of the image 8 and perpendicular to the optical system axis 20. The median plane 13a of the lens 9 is then parallel to the image plane 7. Thus the image 8 is transferred to the input layer 10 in such a way that it is focussed in the longitudinal direction 13 and is defocussed in a direction perpendicular thereto in conformity with the dimension of the input layer 10 in the line direction 14 of the image pick-up tube 11. On the output 15 of the image pick-up tube 11 electrical output signals characteristic of the absorption of the irradiated body slice 4 are available. The signals are obtained by line-by-line scanning of the image points, which have been defocussed in the line direction. The output signals obtained per line are applied to averaging means (not shown), for example a low-pass filter to generate an average output signal.

Figure 2:
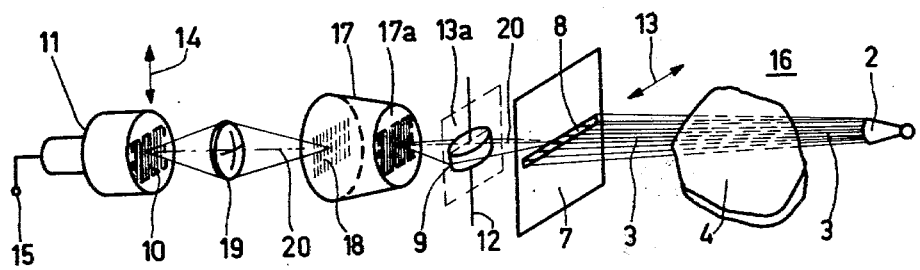
FIG. 2 is further X-ray apparatus with a cylindrical lens followed by an optical image intensifier.

FIG. 2 shows X-ray apparatus 16, in which the X-ray beam 3 is incident, after passage through the body slice 4, onto an X-ray fluorescent screen which represents an image plane 7. The screen converts the X-rays into visible radiation, so that a visible strip-shaped image 8 of comparatively low intensity is formed in the image plane 7. The image 8 is first transferred to an input window 17a of an optical image intensifier 17 by means of a lens 9 which produces an astigmatic optical path, for example a cylindrical lens. The visible output image 18 of the optical image intensifier 17 is then projected onto the input layer 10 of the image pick-up tube 11 by means of a spherical lens 19.

The degree of focussing and defocussing of the image 8 in directions which are perpendicular to each other, and thus the size of the illuminated area of the light-sensitive input layer 10, is adjustable by shifting the optical and electronic components along the optical system axis 20.

Figure 3:
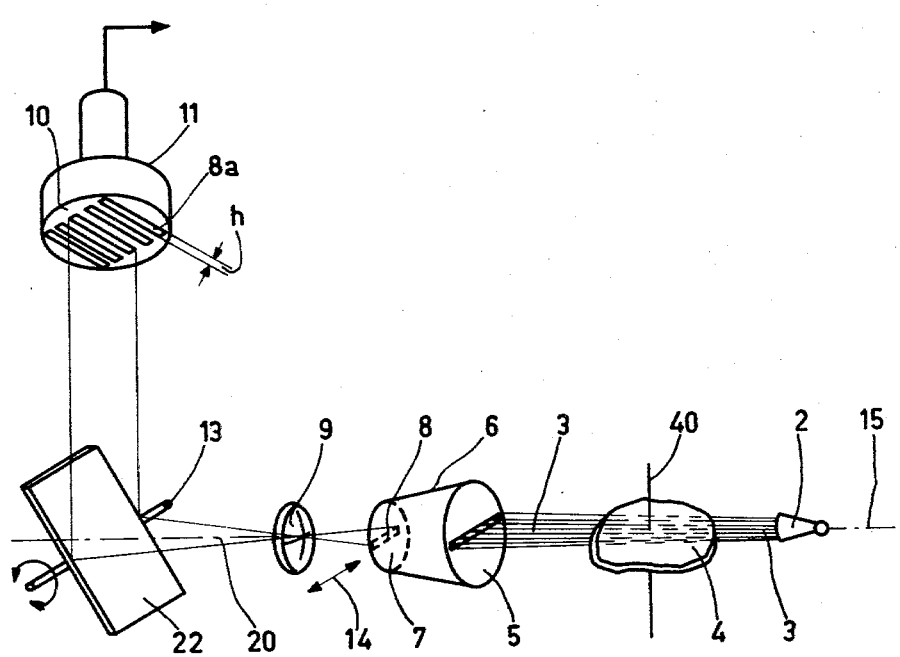
FIG. 3 is X-ray apparatus comprising a plane mirror which serves as a light-deflecting element.

FIG. 3 shows a similar X-ray apparatus which is rotatable about an axis 40 which extends perpendicularly to the body slice 4. In the output image plane 7 of the X-ray image intensifier 6 a strip-shaped visible image 8 is formed which corresponds to the cross-section of the X-ray beam 3, which image is considerably reduced relative to the cross-section of the X-ray beam 3 which is incident on the input face 5 of the X-ray image intensifier 6. Behind the X-ray image intensifier 6 there is disposed a lens system 9, for example a spherical biconvex lens, as well as an image pick-up tube 11 provided with a light-sensitive input layer 10, a plane mirror 12 which serves as light-deflecting element being arranged between the lens system 9 and the image pick-up tube 11, which mirror is rotatable about an axis 13. The axis 13 is then disposed in the plane defined by the longitudinal direction 14 of the image and the optical system axis 15, and parallel to the longitudinal image direction 14, whilst the surface of the plane-mirror 12 is parallel to the axis 13.

By means of the plane mirror 12 the images 8 which consecutively appear in the output image plane 7 of the X-ray image intensifier 6 can be imaged on the light-sensitive input layer 10 of the image pick-up tube 11 so that their longitudinal sides are disposed parallel to and spaced from each other, by continuously rotating the plane mirror 12 about an axis 13. The images 8 are then each time imaged onto one line of the image pick-up tube 11, the height h of the transmitted images 8a on the input layer 10 corresponding at least approximately to the line width of the image pick-up tube 11. FIG. 1 shows only five transmitted images 8a on the input layer 10. However, in practice considerably more images may be transferred to the input layer 10.

Figure 4:
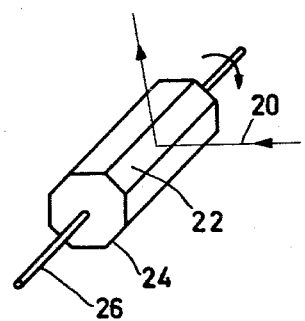
FIG. 4 is a light-deflecting element which takes the form of a polygonal mirror.

FIG. 4 shows a polygonal mirror 16 which serves as light-deflecting element, which mirror rotates about its longitudinal axis 17 with constant angular velocity. Its plane faces 18 are then disposed parallel to the longitudinal axis 17, whilst the longitudinal axis 17 is disposed in the plane which is defined by the longitudinal image direction 14 and the optical system axis 15. The light rays 19 of the images 8 which are consecutively incident on the polygonal mirror 16 are reflected by the consecutive faces 18, the angular velocity of the polygonal mirror 16 being selected so that for given time intervals between the individual images 8 the desired shift of the transmitted images 8a on the light-sensitive input layer 10 of the image pick-up tube 11 is obtained.

Figure 5:
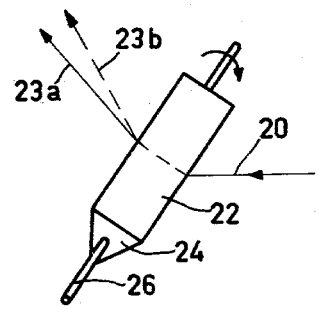
FIG. 5 is a light-deflecting element which takes the form of a prism.

FIG. 5 shows a triangular prism 20 serving as light-deflecting element, which prism is rotatable about its longitudinal axis 21. Its plane sides 22 are disposed parallel to the longitudinal axis 21, the longitudinal axis 21 being disposed in the plane defined by the longitudinal image direction 14 and the optical system axis 15. The light rays 19 of the images 8 which are consecutively incident on the triangular prism 20 are each time refracted by the same side 22, so that the individual images 8 are deflected in different directions 23a and 23b, in such a way that the transmitted images 8a on the light-sensitive input layer 10 of the image pick-up tube 11 are disposed parallel to and spaced from each other. For this purpose, the rotation of the triangular prism 20 is suitably synchronized with the rotation of the X-ray apparatus 1 about the axis 4a.

In the case that the time interval between the images 8 which are incident on the light deflecting element 12, 16, 20 is not constant, especially if the X-ray source 2 is flashed depending on the position of the X-ray apparatus 1 which is moved non-uniformly relative to the body 4, or if the movement of the light-deflecting element 12, 16, 20 is subject to fluctuations, the individual images 8 are projected onto the input layer 10 of the image pick-up tube 11 at different distances from each other. A satisfactory accuracy of the scanning of the transmitted images 8a by means of the electron beam can then still be obtained in that the deflection of the electron beam is corrected. At the instant of each projection (X-ray flash) the light-deflection angle actually produced by the light-deflecting element 12, 16, 20 is measured and electronically compared with a set of reference deflection angles, which are representative of the desired positions of the individual images 8a on the light-sensitive input layer 10 for a known distance of the input layer 10 from the light-deflecting element 12, 16, 20. By comparing the actual light deflection angle with the reference deflection angles error signals are obtained, which represent the deviation of the images 8a from the desired positions. During scanning of the individual images 8a the error signals may be applied to the electron beam deflection system of the image pick-up tube 11, so that in this way the images 8a stored in the input layer 10 can be read correctly.

For such a correction of the electron beam deflection it is necessary that the distance between the individual images 8a on the light-sensitive input layer 10 of the image pick-up tube 11 is selected so large that adjacent images 8a never overlap each other.

A different method of controlling the light-deflecting element 12, 16, 20 is given in German Offenlegungsschrift No. 24 17 234. By means of an additional reference beam (laser beam) the position of the light-deflecting element 12, 16, 20 can be measured in that after reflection or refraction on the light-deflecting element 12, 16, 20 the reference beam is incident on a detector array comprising light detectors (for example photodiodes). The position of a light detector may then correspond to for example the beginning (first line) of an image on the light-sensitive input layer 10 of the image pick-up tube 11. As the reference beam is incident on the light detector a trigger pulse may be generated, which in its turn causes the X-ray source 2 to flash. The rotation of the light-deflecting element 12, 16, 20 and that of the X-ray apparatus 1 about the axis 40 are then also synchronized in such a way that between the individual trigger pulses from the light detectors a sufficiently large angle of the measuring arrangement can be covered between the individual projections.

What is claimed is:

1. In X-ray apparatus for computed tomography, in which strip-shaped visible images in an image plane correspond to individual projections of X-ray exposures and are transferred along an optical axis to a light-sensitive input layer of an image pick-up tube by optical means, the improvement wherein:
the optical means comprises first lens means which function to produce an astigmatic optical path between the image plane and the light-sensitive input layer of the image pick-up tube so that the visible images are focussed in the longitudinal direction of the strip and are defocussed perpendicular to the longitudinal direction of the strip.

2. The improvement of claim 1 wherein the first lens means comprise a planoconvex cylindrical lens having a cylinder axis disposed perpendicular to the longitudinal direction of the strip and to the optical axis.

3. The improvement of claim 1 wherein the first lens means comprise a biconvex cylindrical lens having a cylinder axis disposed perpendicular to the longitudinal direction of the strip and to the optical axis.

4. The improvement of claims 1, 2 or 3 wherein the pick-up tube is adapted for reading out images along a series of parallel lines on the input layer and wherein the optical means function to transfer the image so that the longitudinal direction of the strips is parallel to the lines.

5. The improvement of claims 1, 2 or 3 further comprising
an optical image intensifier disposed between the first lens means and the pick-up tube and
second spherical lens means which function to transfer an image from an output of the optical image intensifier to the input layer of the pick-up tube.

6. The improvement of claim 4 further comprising
an optical image intensifier disposed between the first lens or means and the pick-up tube and
second spherical lens means which function to transfer an image from an output of the optical image intensifier to the input layer of the pick-up tube.

7. In X-ray apparatus for computed tomography in which strip-shaped visible images in an image plane correspond to projections of individual X-ray exposures and are transferred along an optical axis to a light sensitive input layer of an image pick-up tube by optical means, the improvement wherein:
the optical means include light deflecting means which function to consecutively image individual strip shaped images on the input layer of the image pick-up tube so that the strips are parallel and are spaced, one from the other.

8. The improvement of claim 7 wherein the light deflecting means comprise a mirror having a plane surface, the mirror being rotatable about an axis of rotation which is parallel to the plane surface, the axis of rotation being disposed parallel to the plane defined by the longitudinal direction of the strips and the optical axis.

9. The improvement of claim 7 wherein the light deflecting means comprise a rotatable polygonal mirror having plane faces aligned parallel to a longitudinal axis of rotation thereof, the longitudinal axis being disposed parallel to the plane defined by the longitudinal direction of the strips and the optical axis.

10. The improvement of claim 7 wherein the light deflecting element comprises a prism having plane sides which are aligned parallel to a longitudinal axis, the prism being rotatable about the longitudinal axis, the longitudinal axis being disposed parallel to the plane defined by the longitudinal direction of the strips and the optical axis.

* * * * *